United States Patent
Carr, Jr.

(10) Patent No.: US 7,202,048 B2
(45) Date of Patent: Apr. 10, 2007

(54) ONSET OF FORCE DEVELOPMENT AS A MARKER OF THROMBIN GENERATION

(75) Inventor: Marcus Carr, Jr., Midlothian, VA (US)

(73) Assignee: Hemodyne, Inc., Bethesda, MD (US)

( * ) Notice: Subject to any disclaimer, the term of this patent is extended or adjusted under 35 U.S.C. 154(b) by 635 days.

(21) Appl. No.: 10/405,472

(22) Filed: Apr. 3, 2003

(65) Prior Publication Data

US 2003/0199428 A1     Oct. 23, 2003

Related U.S. Application Data

(60) Provisional application No. 60/387,409, filed on Jun. 11, 2002, provisional application No. 60/369,559, filed on Apr. 4, 2002.

(51) Int. Cl.
*C12Q 1/56* (2006.01)

(52) U.S. Cl. .......................... 435/13; 435/69.6; 436/69

(58) Field of Classification Search ...................... None
See application file for complete search history.

(56) References Cited

OTHER PUBLICATIONS

Carr et al. Am J Med Sci 1991;302(1)13-18.*
Jen et al. Cell Motility 1982;2:445-455.*
Greilich et al. Am J Med Sci 1994;307(1)15-20.*

* cited by examiner

*Primary Examiner*—Ralph Gitomer
*Assistant Examiner*—Bin Shen
(74) *Attorney, Agent, or Firm*—Whitham Curtis Christofferson & Cook, P.C.

(57) ABSTRACT

Platelet contractile force (PCF) is used as a surrogate marker of thrombin generation. PCF generation occurs concomitant with the burst of prothrombin fragment F 1+2 release. The time between assay start and PCF onset is identified as the thrombin generation time (TGT), and is used in assessing risk of bleeding, in diagnosing various disorders, and in monitoring the effects of pharmaceutical and other treatments. TGT is prolonged in clotting factor deficiencies and in the presence of direct and indirect thrombin inhibitors. TGT shortens to normal with clotting factor replacement and shortens with administration of rVIIa. TGT is short in thrombophilic states such as coronary artery disease, diabetes and thromboangiitis obliterans and prolongs toward normal with oral and intravenous anticoagulants.

8 Claims, 9 Drawing Sheets

ONSET OF FORCE DEVELOPMENT AS A MARKER OF THROMBIN GENERATION

This application claims priority to provisional U.S. Application 60/369,559 filed Mar. 4, 2002, and provisional U.S. Application 60/387,409 filed Jun. 11, 2002.

BACKGROUND OF THE INVENTION

1. Field of the Invention

The invention is related to a method, instrumentation, and treatments which use the onset of platelet contractile force (PCF) as a surrogate marker thrombin generation.

2. Description of the Prior Art

Thrombin generation is increasingly recognized as the critical component of normal hemostatic function. If thrombin formation is delayed as in various clotting factor deficiencies the individual is at risk for excessive bleeding. If thrombin generation is too rapid or incompletely controlled, as in thrombophilic states, the patient is at risk for recurrent thrombosis. Therapeutic interventions in both cases are geared at reversing abnormal thrombin generation either by speeding it up with hemostatic agents or slowing it down with anticoagulants.

Routine coagulation screens such as the prothrombin and partial thromboplastin time use fibrin formation as a surrogate marker of thrombin generation. Unfortunately, these studies are routinely performed in platelet poor plasma and thereby miss the potential effects of cellular elements on the rate of thrombin formation. The critical role played by tissue bearing cells and activated platelets is increasingly recognized (1,2). The continuing development of potent antiplatelet and anticoagulant agents and their combined application in settings such as acute coronary syndromes and cerebrovascular attacks have emphasized the need for a global measure of thrombin generation which could reflect the combined effects of these agents.

SUMMARY OF THE INVENTION

It is an object of this invention to provide a simple, real-time assay of thrombin generation in whole blood.

It is another object to provide an assay for thrombin generation which can utilize any enzyme which will clot fibrinogen without activating platelets (e.g., reptilase, batroxibin, or other snake venom derived proteins, etc.).

According to the invention, the assay is based on the absolute thrombin dependence of platelet contractile force (PCF). We have previously reported that PCF is reduced by some clotting factor deficiencies (3), and in the presence of a variety of anticoagulants (4,5,6). The reduction in PCF is at least partially due to delayed onset of PCF development. In this invention, it is has been found that the onset of PCF occurs simultaneously with the appearance of prothrombin fragment 1+2 (F 1+2). Thus, the time interval from the moment of assay initiation to the moment of initial force detection, referred to herein as Thrombin Generation Time (TGT), may be used as an assay for risk assessment, diagnosis, and drug monitoring. The utility of TGT as an assay has been demonstrated by abnormalities in a variety of patients, and by dose dependent changes induced by a variety of therapeutic agents. Therefore, the TGT assay has potential as both a diagnostic and drug monitoring assay.

BRIEF DESCRIPTION OF THE DRAWINGS

The foregoing and other objects, aspects and advantages will be better understood from the following detailed description of the preferred embodiments of the invention with reference to the drawings.

Composite PCF kinetic curve plots data as the mean ± the standard deviation for each data point.

DETAILED DESCRIPTION OF THE PREFERRED EMBODIMENTS OF THE INVENTION

Current routine hemostatic laboratory tests ignore the contribution of platelets and other cellular elements to normal clot formation. The prothombin time (PT) and partial thromboblastin time (PTT) are generally performed on samples of platelet poor plasma and substitute phospholipid for the absent platelet membranes. While these assays have proven utility in the diagnosis of clotting factor deficiencies and monitoring of heparin and warfarin anticoagulation, they are not adequate for monitoring the response to some of the newer anticoagulant and hemostatic agents. The PTT is generally insensitive to the effects of low molecular weight heparin (11) and the PT does not reflect the therapeutic potential of recombinant factor VIIa (12). Since both assays are performed in the absence of platelets, they do not have the potential to evaluate the "anticoagulant" effects of some of the new potent antiplatelet agents.

The generation of thrombin is now recognized as the critical step of hemostasis. In the past, the coagulation mechanism was typically portrayed as a cascade of fluid phase enzyme reactions leading to the production of the fibrin clot. Now, the process is divided into initiation, amplification and propagation phases. Clotting is initiated on a tissue bearing cell, but the initial thrombin produced is insufficient to support clot formation. The initial thrombin signal is amplified by the production of several multi-component protease complexes on the surface of activated platelets. The thrombin that results from this amplification step is sufficient to cause additional platelet activation, fibrin clot formation and propagation of the clotting process through out the damaged region. It is now recognized that the bleeding in hemophilia is due to a deficient amplification step, which causes deficient platelet activation in the wound area (13–16). While routine coagulation tests continue to be of use, they do not adequately reflect coagulation events as they are presently understood.

The TGT assay, described herein, has several potential advantages. First, it is performed on whole blood antico-aguated with citrate. The sample does not have to be run immediately and the sample tubes routinely used in coagulation testing are adequate sample sources. Since the blood does not have to be separated into plasma and cells, less time is required for processing and near patient monitoring is thus facilitated. Second, the assay yields a rather global evaluation of clotting function. The TGT measures the adequacy of clotting factor and platelet interactions, clot elastic modulus development assesses clot formation and strength, and PCF provides an independent marker of platelet function (7–9). Third, the assay appears to correlate with abnormalities at both extremes of measurement. Rapid thrombin generation is seen in several recognized hypercoagulable states (17–21), and delayed thrombin formation is seen in a variety of well documented bleeding disorders (3,22,23). The assay is sensitive to a full range of anticoagulant (4,5,6,24,25) and hemostatic agents (26). Finally, the assay can employ a range of initiation steps to include enzymes such as batroxibin or other snake venom derived proteins, or simply recalcification.

Alternative methods of assessing thrombin generation are available and newer techniques are under development. Previous markers of thrombin activity have relied on either detection of F 1+2 or the thrombin-antithrombin complex (TAT). Each of these markers is limited in terms of its ability to monitor ongoing thrombin generation. Both assays tend to be static, one moment in time, snap shots of thrombin activity. Neither assay truly measures thrombin activity, but both indicate that prothrombin activation has occurred at some point in the sample tested. Two recent assays offer the potential for measuring both the onset of thrombin production and the total amount produced in the sample. The Thrombogram™ uses a 96-well microtiter plate and a fluorometer to measure the change in fluorescence as thrombin cleaves a fluorogenic substrate (27). Measurements can be made on either platelet poor or platelet rich plasma and a software package (Thrombogram™, Synapse BV) produces a kinetic curve of thrombin concentration (nM) versus time. The system is capable of detecting delayed thrombin generation in hemophilia, but the test cannot be performed on whole blood. Similar techniques have used chromogenic substrates to monitor thrombin generation in plasma, but the chromogenic signal is masked in whole blood samples. Thrombin generation can be accomplished in whole blood by repetitively sampling and using an antibody to assay for α-human prethrombin-1 (2).

Several instruments hold potential as monitors of whole blood clotting due to their ability to measure changes in clot mechanical properties. The thromboelastogram (TEG®, Haemoscope) was initially described in 1948 (28) and continues to used in various formats to assess clotting of whole blood (29–31). It measures the degree of coupling between a stationary inner piston and a rotating outer cup during clot formation. Coupling first occurs when clot begins to form in the sample space between the inner and outer surfaces. Once clotting is complete, the degree of coupling is related to the structural integrity of the clot. The TEG® R-parameter has been shown to be sensitive to the effects of rVIIa in blood from patients with clotting factor deficiencies (32). The ROTEG® (Pentapharm, Munich, Germany) is a recent modification of the original TEG technology. In the ROTEG®, the inner cylinder rotates and the outer cup is stationary (33). Like the TEG, the ROTEG assesses coupling of the inner and outer cylinders during clotting. The ROTEG output is virtually identical to the TEG, but it has the capability to measure four samples at once and it is less sensitive to vibration. Sensitivity to the effects of rVIIa in whole blood has been demonstrated (34). The Sonoclot is another instrument, which measures viscoelastic properties of blood during clotting (35,36). A hollow tube is caused to vibrate up and down within a cup containing the clotting sample. Prior to clotting, the resistance to oscillation is used to measure sample viscosity. Once clotting begins, changes in the signal are nonquantitatively interpreted as reflecting various clotting events. The onset of clotting can be detected and therefore should correlate with the onset of thrombin production. A much more quantitative approach is offered by the ReoRox® (MediRox, Linkoping, Sweden) which measures shear modulus, loss modulus, phase angle, damping and frequency of a sample held between an oscillating outer cup and an inner probe (37). Onset of clotting and clot completion time are measured as well as the elastic properties of the resultant clot. No published data are available correlating thrombin generation to the onset of clotting in this instrument, but one would anticipate that a reasonable correlation should exist.

Figure 9:
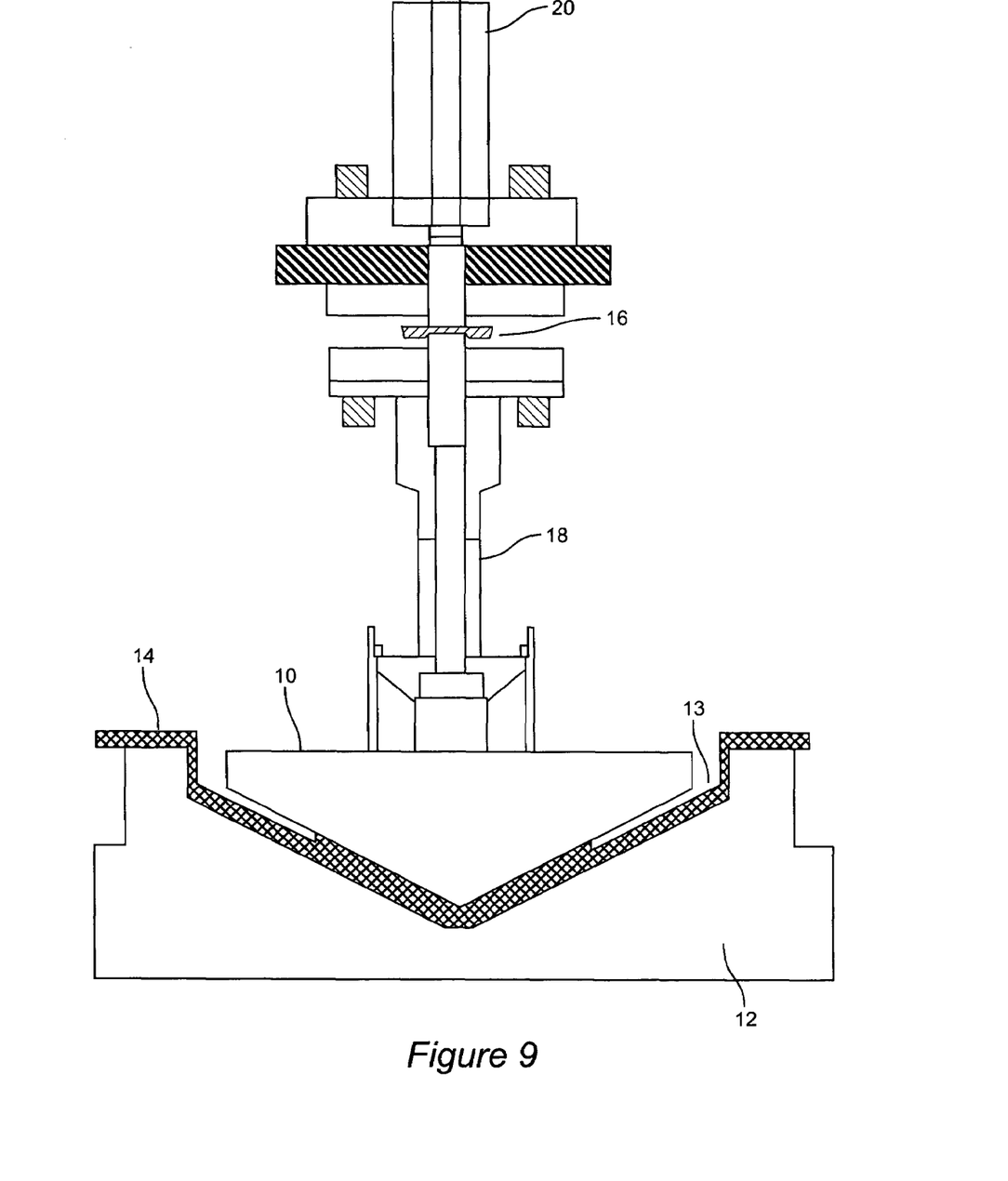
FIG. 9. This is a schematic diagram of an exemplary sample holder for blood samples in which TGT measurements may be made.

The Hemodyne® platelet analysis system, as is described in U.S. Pat. Nos. 4,986,964, 5,205,159, and 5,293,772, each of which are herein incorporated by reference, is the preferred instrument for measuring TGT (or onset of platelet contractile force), within the practice of this invention. In this device, the blood sample is positioned in a chamber that is contacted by a top plate. PCF is measured by the clot forming and pulling the top plate towards chamber. However, it should be understood that other devices which measure platelet contractile force, may be used to identify the TGT within the context of this invention. FIG. 9 depicts a sample holder similar to that described in the above-identified patents which includes a sample cone 10 separated from a heating block 12 lined with a disposable sample cup 14. A blood sample is deposited on the sample cup 14 and is contacted by the sample cone 10. PCF measurements are made using a displacement transducer 16 connected to the sample cone 10 by shaft 18. A solenoid 20 is used in the measurements as described in U.S. Pat. Nos. 5,205,159 and 5,293,772.

In summary, the invention contemplates using an instrument for measuring thrombin generation time (TGT) in whole blood. The technique uses the onset of platelet contractile force (PCF), a thrombin dependent process, as a marker of thrombin formation. The technique is reproducible and yields a relatively tight normal range for asymptomatic volunteers. This range is preferably 300 to 500 seconds, but may vary within the practice of this invention. The onset of PCF occurs at the moment of F 1+2 burst. Therefore, the invention may be used to assess and monitor a number of different clinical matters. For example, a patient's risk of bleeding may be identified when his or her TGT is longer than the normal range for TGT.

Similarly, it has been found that the onset of PCF is delayed in patients with deficiencies of clotting factors VIII and IX (i.e., they have a longer TGT(3)). TGT appears to be short in patients with coronary artery disease and diabetes and is sensitive to the effects of multiple anticoagulants (4,5,6,24,25) and antiplatelet medications.

The combination of TGT, PCF and clot elastic modulus CEM measurements on a single, small sample of whole blood provides a potential global measure of hemostasis. U.S. Pat. No. 5,205,159 describes a method for measuring both clot elastic modulus and force development from the same blood sample, and is herein incorporated by reference. In preparing a more global measure of hemostasis, the TGT would be determined as described herein, and the PCF and CEM would be determined as described in U.S. Pat. No. 5,205,159.

The assay has potential for documentation of the correction of deficient thrombin generation by hemostatic agents such as recombinant FVIIa (26). In operation, a therapeutic agent, e.g., a clotting factor such as Factor VIII (Recombinate™ by Baxter, ReFacto™ by Wyeth-Ayerst, Kogenate™ by Bayer, etc.), Factor IX (Mononine™ by Baxter, Benefix™ by Wyeth-Ayerst, etc.), and Factor VII (Recombinante Factor VIIa Novoseven™ from Novo-Nordisk, etc.) would be provided to a patient whose TGT is below the normal range, and, periodically his TGT would be re-measured until TGT returned to normal. Conversely, anticoagulants such as unfractionated heparin, low molecular weigh heparin (e.g., Lovonox, Fragmin, Anti-XA, Axrista, etc.), hirudin, refludin, bivalirudin, warfarin, coumadin, etc., could be administered to a patient at risk for coronary artery disease, stroke, deep venous thrombosis, etc., and periodic monitoring of TGT can be used to assess when a therapeutic range of TGT has been reached (i.e., TGT has returned to the normal range (300 to 500 seconds; 350–450 seconds; 375–400 seconds). Reversal of these anticoagulants can be monitored by the same process. In similar fashion, the effects of anti-platelet medication such as aspirin, ticlopidine, clopedrigil, abciximab (e.g., ReoPro™ by Eli Lilly), integrilin, and aggrastat, on thrombin generation can be monitored or measured so as to determine whether TGT is in or has returned to the normal range.

EXAMPLE

Materials and Methods

The patients and normal controls in this study were enrolled under a series of protocols approved by the Institutional Review Board for Human Studies of Virginia Commonwealth University. Written consent was obtained from each volunteer. Blood was obtained via aseptic venipuncture into evacuated tubes containing 3.2% sodium citrate.

Batroxobin was purchased as Atroxin®, Bothrops atrox venom protein (Sigma Diagnostics), was dissolved in deionized water, and used without further purification. It was maintained on ice and used within 3 hours of being prepared. Calcium chloride was purchased as analytical grade purified salts. Nanopure water was used in the preparation of all solutions.

Porcine heparin (1,000 USP U/ml was purchased as a sterile solution from LyphoMed® (Rosemont, Ill.). It was used without modification. Hirudin from leeches was purchased from Sigma Diagnostics (St. Louis, Mo.). Bivalirudin was generously provided by The Medicines Company (Cambridge, Mass.). Kogenate® was obtained from Bayer Corporation (Elkhart, Ind.). Recombinant factor VIIa (NovoSeven®) was generously provided by Novo Nordisk (Copenhagen, Denmark).

Whole blood clot formation was induced by the addition of $CaCl_2$ or a combination of $CaCl_2$ and batroxobin (0.21 µg/ml). Platelet contractile force development and clot elastic modulus were measured for 1200 seconds.

Measurement of Platelet Contractile Force:

The Hemodyne® hemostasis analyzer (Hemodyne, Inc., Richmond, Va., USA) measures forces generated by platelets within a clot formed between a thermostated cup and parallel upper plate (7,8). Before clotting, the upper plate is centered above the cup and lowered into the sample. As the clot forms, it attaches to the inner walls of the cup and the bottom of the upper plate. The entire sample volume is contained between the upper and lower surfaces. Once fibrin is formed, platelets within the network pull fibrin strands inward transmitting force through the network to the surfaces to which the clot is adherent. Force measurement is accomplished utilizing a transducer coupled to the upper plate. As platelets contract, the transducer produces an electrical output proportional to the amount of force generated. The transducer output is continuously recorded.

Measurement of Clot Elastic Modulus:

Clot elastic modulus was measured by applying a downward force of known magnitude to the upper plate of the Hemodyne apparatus (9). The amount of downward displacement caused by the force was measured. The ratio of downward force (stress) to downward displacement (strain) was used to calculate the elastic modulus. Stress equals the force applied divided by the area of application and strain is the degree of shape change induced by the applied force.

Figure 1:
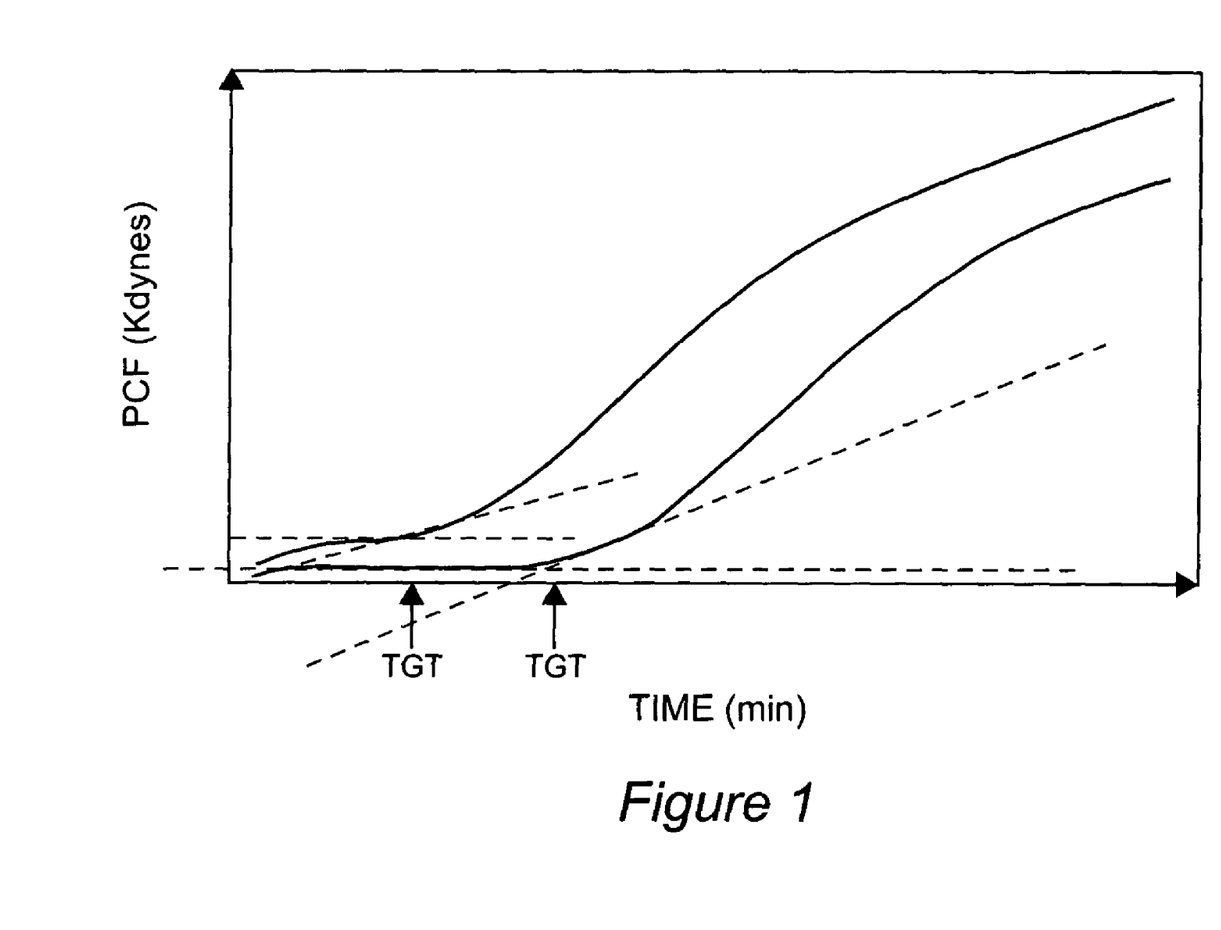
FIG. 1. Determination of the thrombin generation time (TGT) from the kinetics of platelet contractile force (PCF) development after addition of calcium (10 mM final) and batroxobin (0.21 µg/ml final) to 700 µl of citrated (3.2%) whole blood at time zero. The TGT is taken to be the initial inflection point of the PCF curve, ie. the moment the PCF first begins to increase.

Determination of the Thrombin Generation Time (TGT):

Citrated blood clotted with batroxobin, or other similar enzymes (e.g., reptilase), and calcium develops PCF. Since batroxobin does not activate platelets, there is a lag phase prior to the onset of PCF in the batroxobin system. During this time period, thrombin is generated by re-calcification. Since the fibrin network is in place prior to the generation of thrombin, PCF becomes apparent as soon as a small amount of thrombin is generated (FIG. 1). Thus, the inflection or take off point in the PCF curve serves as a marker of thrombin generation in the batroxobin mediated assay. For ease in identification, the first derivative of the curve in FIG. 1 will provide a sharp break where the curve increases (TGT being at the spike). The instrumentation used for the analysis, such as that shown in FIG. 9, can provide the output of FIG. 1 or the first derivative for identification of TGT, or, alternatively, the output could simply be an indicator light array indicating when the TGT is in the normal range or outside of the normal range.

We designate the time between calcium addition and initial PCF development the Thrombin Generation Time (TGT). Similar results can be obtained without using a snake venom enzyme if one simply recalcifies the plasma sample. Since thrombin generation must be followed by fibrin clot formation before PCF can begin to occur in the recalcification assay, the lag phase tends to be longer and more variable. Similar assays termed reptilase clot retractions were shown in the early seventies to be sensitive to a variety of antiplatelet and anticoagulant agents (10).

Measurement of prothrombin fragment 1+2:

Citrated whole blood samples were divided into 700 μL aliquots and placed in polypropylene tubes. Clotting was initiated by the addition of $CaCl_2$ (10 mM final). The moment of calcium addition was taken as time zero. Clotting activity was terminated at set one minute intervals in the individual aliquots by the addition of 5 U/ml of heparin. Plasma was obtained by centrifuging the blood aliquots at 2,000 g for 10 minutes. The prothrombin fragment 1+2 concentration of plasma samples was determined by enzyme immunoassay (Enzygnost F 1+2, Dade-Behring, Marburg, Germany) according to manufacturer's instructions.

Statistical Analysis

Data are presented as mean±standard deviation (S.D.). Statistical significance where reported was determined using the student's paired t test for normally distributed values. Differences were considered statistically significant at $p<0.05$.

Results

Figure 2:
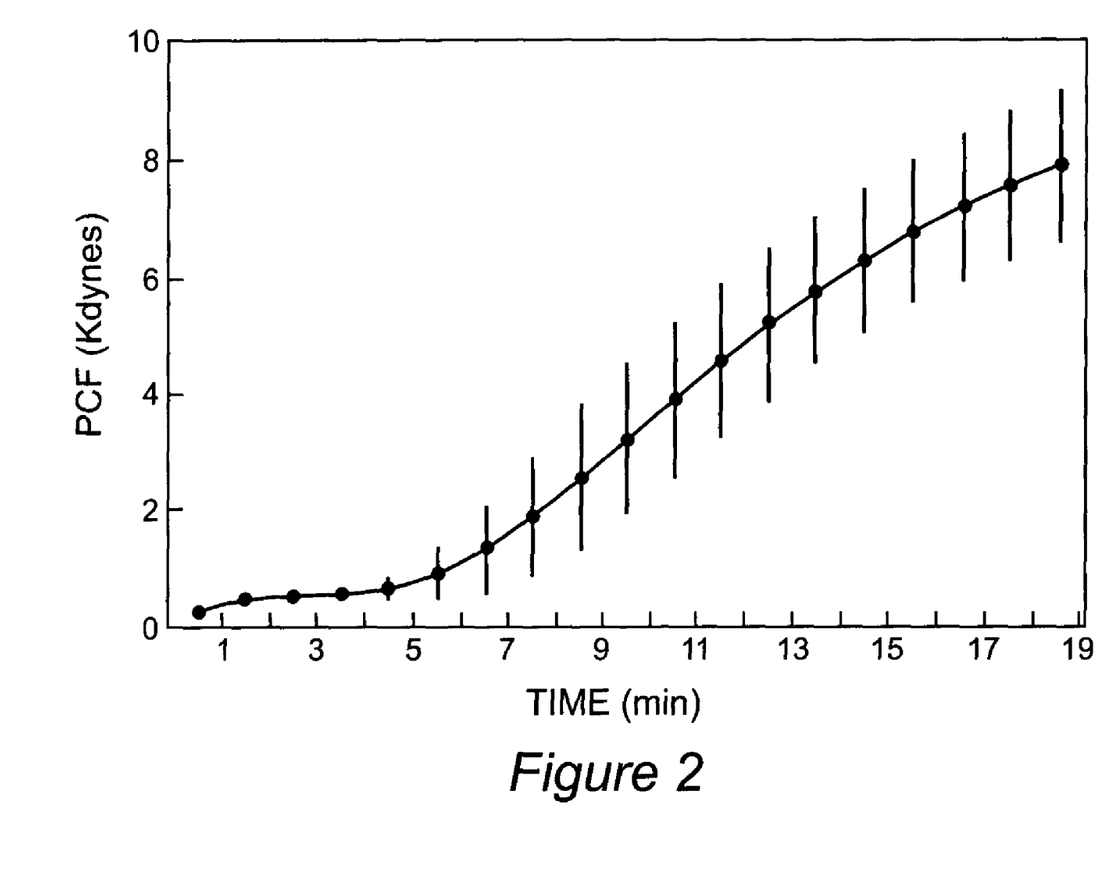
FIG. 2. TGT and PCF values for twenty-five normal volunteers.

Normal Values of PCF, CEM and TGT in Batroxobin Induced Whole Blood Clots:

Twenty-five normal controls were evaluated. Fifteen were males and ten were females. Three were black, four were Asian and 18 were white. The ages ranged from 34 to 56 with an average age of 45±1.16 years. Normals had no evidence for or history of diabetes, coronary artery disease, hypertension or hyperlipidemia and were not on prescription medications. All but one of the normals were nonsmokers. The composite kinetic curve of PCF development with associated standard deviation for each data point is presented in FIG. 2. Mean values for PCF (at 1200 seconds), CEM (at 1200 seconds) and TGT are included in Table 1 (where the PCF value is presented as Kdynes (mean±SEM), the CEM value is presented as Kdynes/$cm^2$ (mean±SEM), and the TGT is presented as seconds (mean±SEM).

TABLE 1

EFFECT OF HEMOPHILIA A, HEMOPHILIA B, AND CORONARY ARTERY DISEASE ON PLATELET CONTRACTILE FORCE, CLOT ELASTIC MODULUS, AND THROMBIN GENERATION TIME IN WHOLE BLOOD

|  | n | PCF | p | CEM | p | TGT | p |
|---|---|---|---|---|---|---|---|
| Normal healthy volunteers | 25 | 7.82 ± 0.27 | — | 18.84 ± 1.13 | — | 392 ± 19 | — |
| Factor VIII Deficiency | 5 | 2.52 ± 0.71 | <0.01 | 7.29 ± 2.66 | <0.01 | 760 ± 147 | 0.07 |
| Factor IX Deficiency | 5 | 1.08 ± 0.16 | <0.01 | 3.75 ± 1.09 | <0.01 | 1064 ± 84 | <0.01 |
| Coronary Artery Diseas | 10 | 11.51 ± 1.18 | <0.01 | 34.07 ± 4.65 | <0.01 | 227 ± 17 | <0.01 |

Figure 3A:
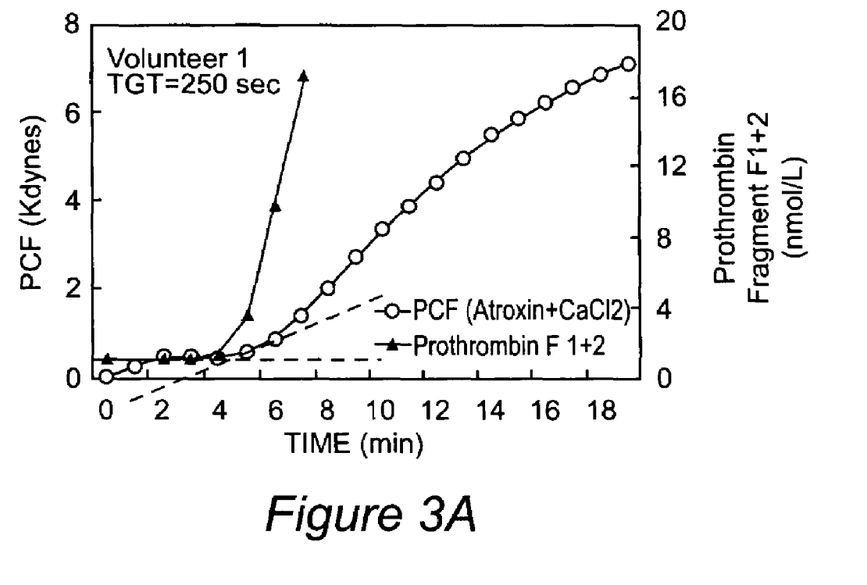
FIGS. 3A and 3B. Prothrombin activation fragment 1.2 release is associated with onset of PCF in whole blood.
Figure 3B:
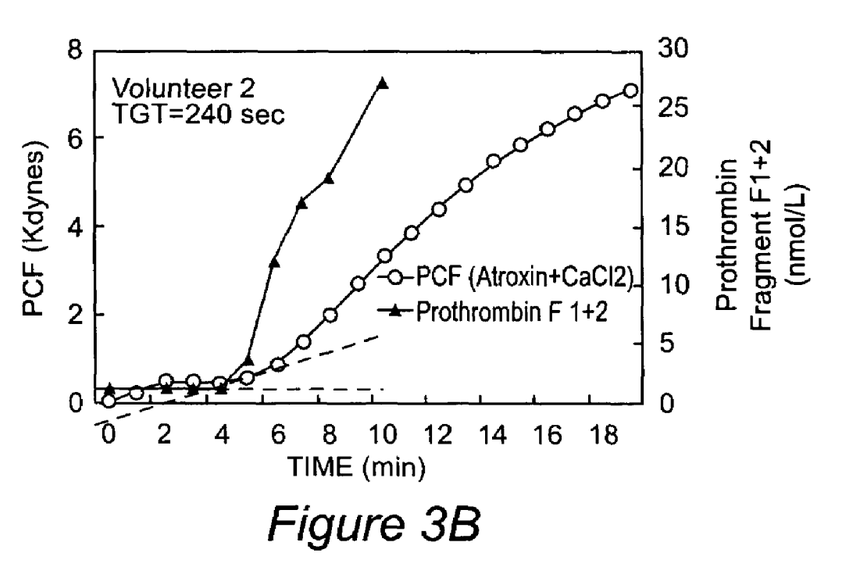

Correlation of TGT with Prothrombin Fragment 1+2 Release in Whole Blood:

Samples of whole blood were obtained from four asymptomatic volunteers. The sample from each individual was divided into aliquots for PCF/TGT determination and F 1+2 measurement. Aliquots for F 1+2 assay were activated by the addition of calcium chloride at time zero. Any clotting activity was terminated at set one minute intervals in individual aliquots by the addition of heparin. The samples were then processed as indicated above. Typical curves for two volunteers are depicted in FIG. 3. The upper curve is for a female and the lower for a male. As can be seen the initial increase in F 1+2 occurs at the same moment as the take off of PCF. Volunteer number 3, a male smoker with history of hypercholesterolemia, had a short TGT of 120 seconds and the initial increase in F 1+2 occurred at 120 seconds. TGT was 180 seconds and take off of F 1+2 was 180 seconds in volunteer number 4, a female with known hypercholesterolemia.

Figure 4:
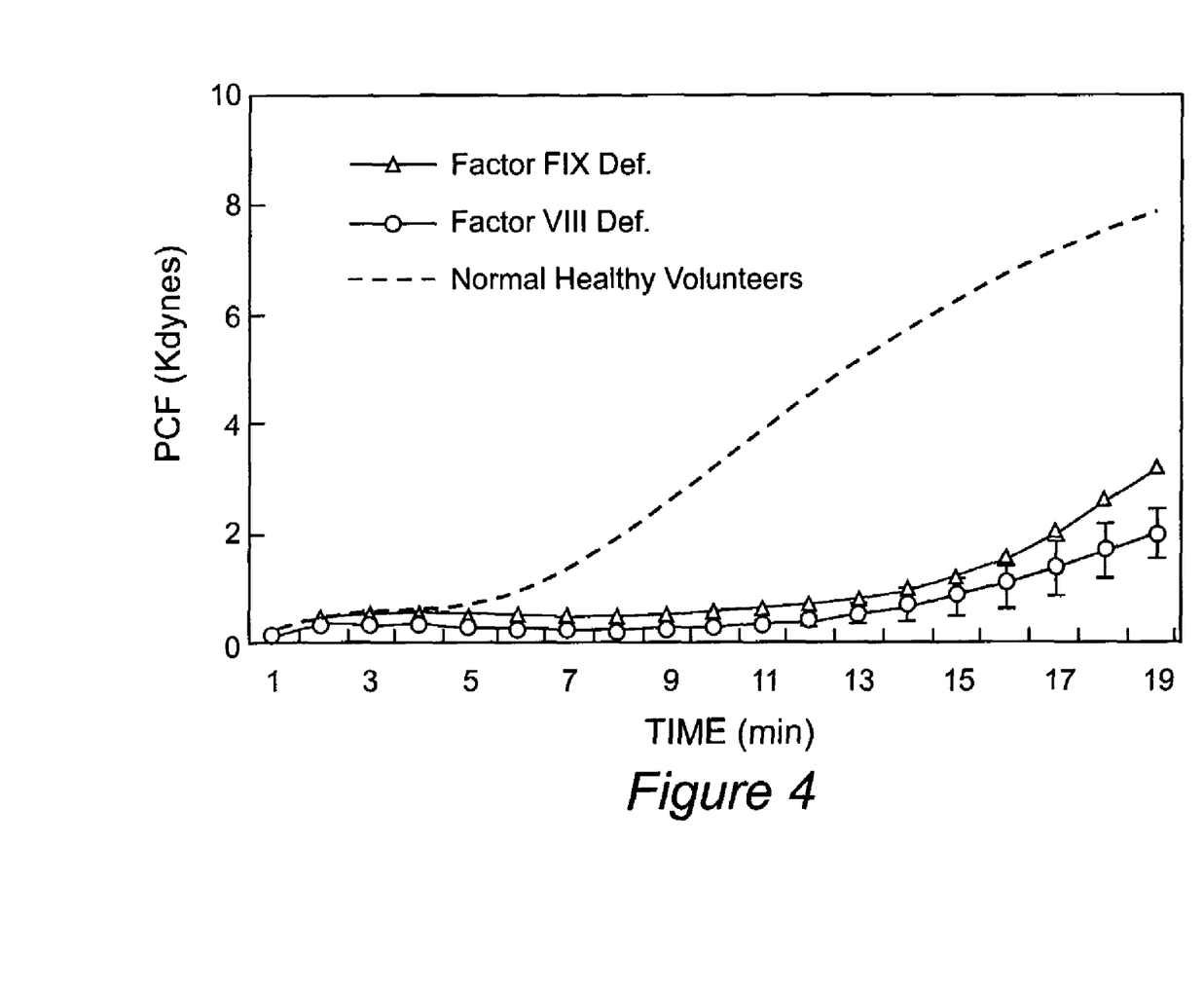
FIG. 4. Effect of factor VIII deficency and of factor IX deficiency on TGT in whole blood. Data are presented as composite PCF kinetics for six patients with hemophilia A and six patients with hemophilia B. Each data point is the mean±SEM. The mean normal PCF curve is included as a dashed line for comparison.

Effect of Factor IX and VIII Deficiencies on TGT:

Five patients with hemophilia B (factor IX deficiency), and five patients with hemophilia A (factor VIII deficiency) were studied. Typical PCF kinetic curves are presented in FIG. 4. As can be seen, the TGT is prolonged and the PCF value after 1200 seconds is reduced. Mean values for PCF, CEM and TGT are included in Table 1.

Figure 5:
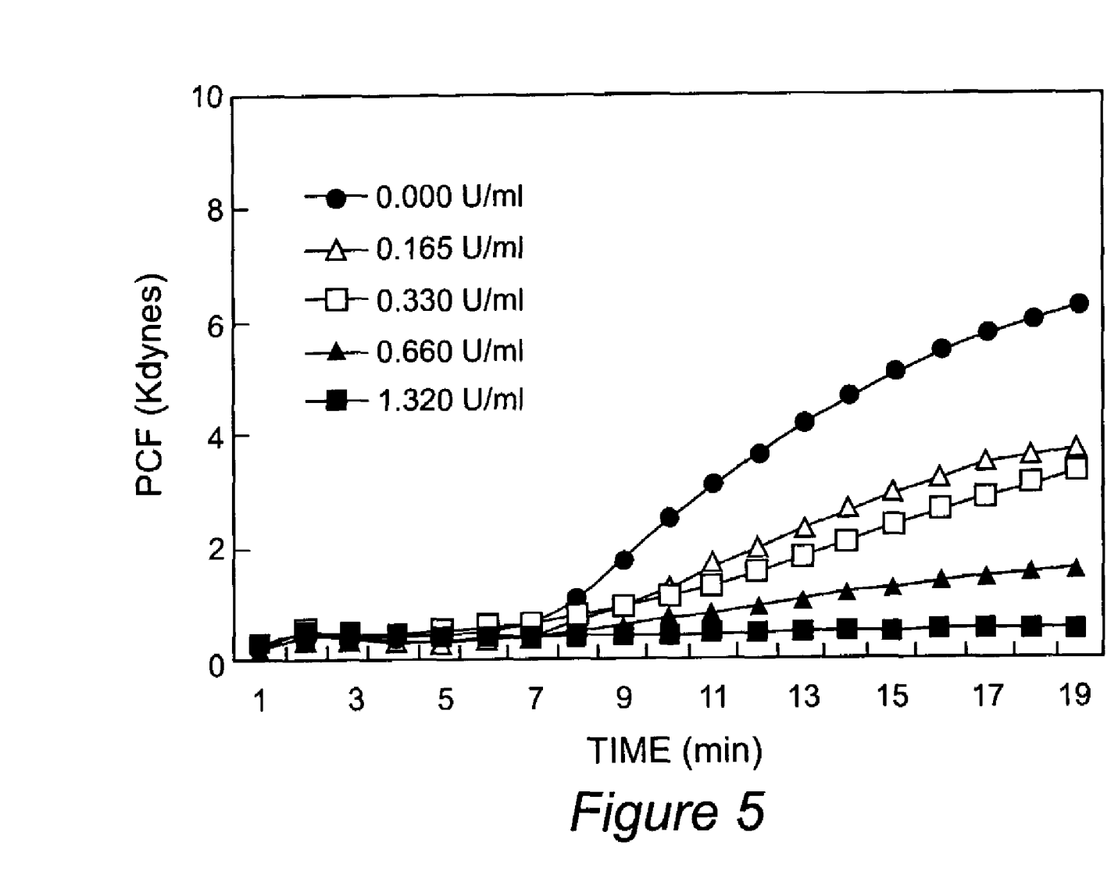
FIG. 5. Effect of a direct antithrombin on TGT. The effects of increasing hirudin concentrations on the kinetics of PCF development in normal whole blood clotted by the addition of batroxobin and calcium. As the hirudin concentration is increased, the TGT prolongs and the PCF declines.

Effect of Anticoagulation on TGT in Normal Blood:

Effects of direct and indirect anti-thrombins were investigated by adding increasing amounts of hirudin (direct) and heparin (indirect-antithrombin III dependent). Both agents produce a dose depend prolongation of the TGT and reduction of PCF. A typical set of data for hirudin is presented in FIG. 5. Similar curves were seen with heparin and reproduced those previously published (4). Values for TGT, PCF and CEM as a function of heparin and hirudin concentration are presented in Table 2 (where PCF is presented as Kdynes, CEM is presented as Kdynes/$cm^2$, and TGT is presented in seconds).

TABLE 2

DOSE DEPENDENT EFFECTS OF DIRECT (HIRUDIN) AND INDIRECT (HEPARIN) ANTITHROMBIN ANTICOAGULANTS IN NORMAL WHOLE BLOOD, AND OF FACTOR VIII CONCENTRATE (KOGENATE) IN FACTOR VII DEFICIENT WHOLE BLOOD

|  | conc. (U/ml) | PCF | CEM | TGT |
|---|---|---|---|---|
| Hirudin | 0.000 | 6.53 | 16.11 | 360 |
| Hirudin | 0.165 | 4.01 | 12.34 | 420 |
| Hirudin | 0.330 | 3.57 | 11.21 | 480 |
| Hirudin | 0.660 | 1.80 | 6.50 | 560 |
| Hirudin | 1.320 | 0.70 | 0.73 | >1200 |
| Heparin | 0.000 | 4.20 | 16.6 | 325 |
| Heparin | 0.100 | 1.90 | 13.04 | 375 |
| Heparin | 1.000 | 0.00 | 0 | >1200 |
| Kogenate | 0.000 | 0.8 | 0.7 | 1200 |
| Kogenate | 0.175 | 2.0 | 5.5 | 827 |
| Kogenate | 0.350 | 2.5 | 8.4 | 500 |
| Kogenate | 0.700 | 3.2 | 10.4 | 407 |
| Kogenate | 1.400 | 4.3 | 13.5 | 347 |

Figure 6:
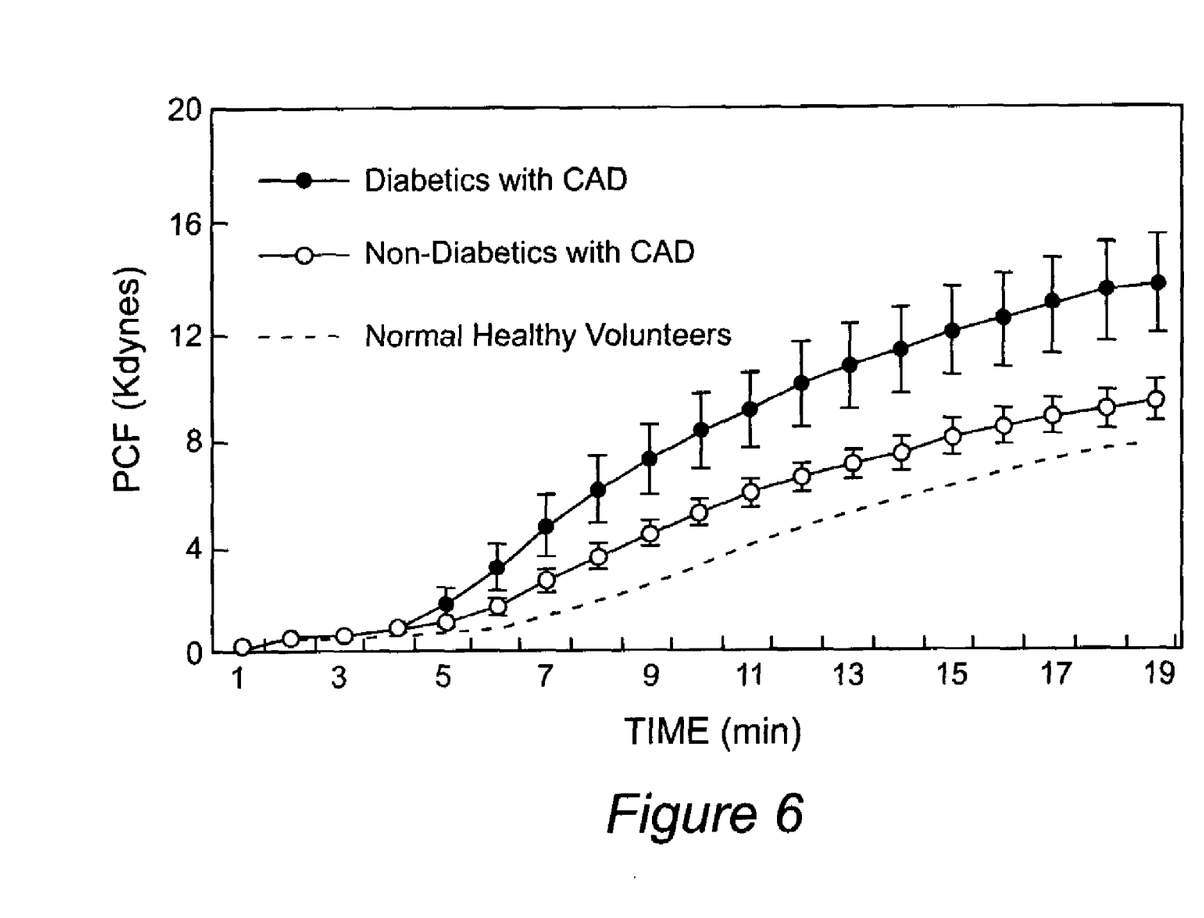
FIG. 6. TGT is shorter and PCF higher in diabetics with coronary artery disease. Data are presented as composite PCF kinetics for five patients with diabetes with critical coronary artery disease demonstrated by coronary angiogram. Each data point is the mean±SEM. The mean normal PCF curve is included as a dashed line for comparison.

TGT in Patients with Coronary Artery Disease with and without Diabetes:

Twenty-five patients undergoing cardiopulmonary bypass grafting were evaluated. Eleven of the patients were found to have diabetes. A composite PCF kinetic curve for five of the diabetic patients is depicted in FIG. 6. TGT is shorter and PCF is higher in these patients when compared to normal. Taking all patients with CAD as a group, mean TGT values are significantly shorter (p<0.01), mean PCF values are significantly higher (p<0.01) and mean CEM values are significantly higher (p<0.01) (see Table 1).

Figure 7:
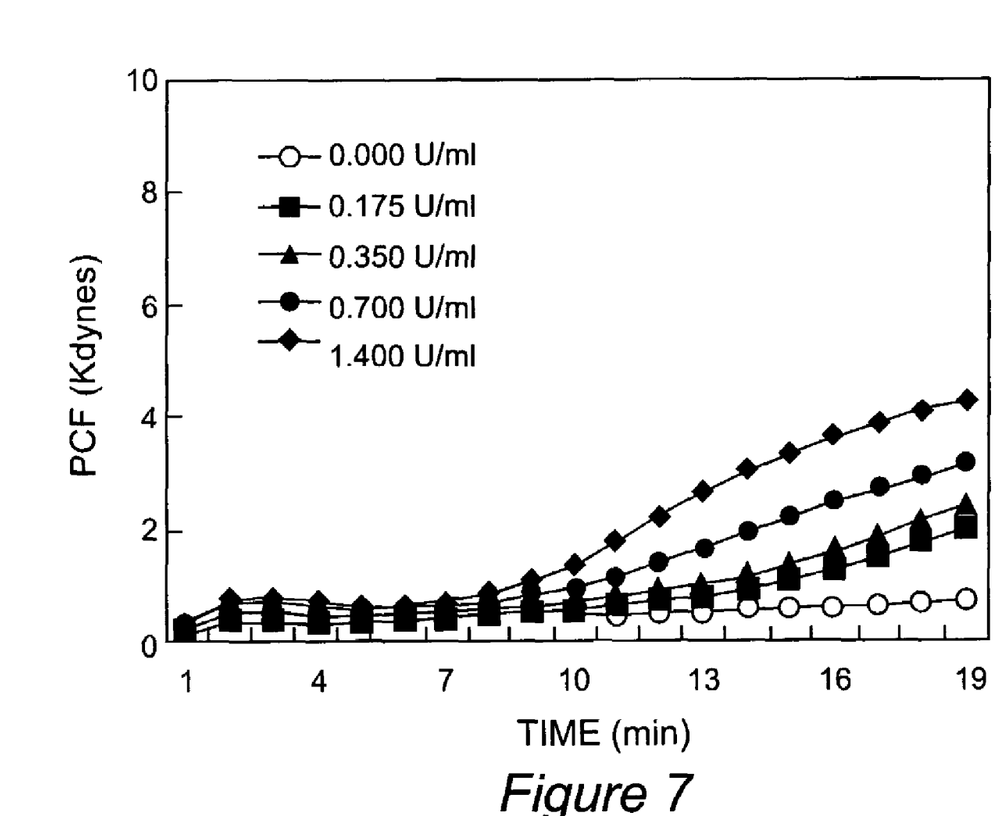
FIG. 7. Factor replacement normalizes the TGT and PCF in blood from patients with hemophilia. The effects of increasing factor VIII concentrations (Kogenate®, Bayer Corp.) on the kinetics of PCF development in normal whole blood clotted by the addition of batroxobin and calcium. As the factor VIII concentration is increased, the TGT shortens and the PCF increases.

Effect of Factor Replacement on TGT in Hemophilia A:

As noted above, TGT is prolonged and PCF reduced in hemophilia A and B. The effects of factor replacement were studied in three factor VIII deficient and three factor IX deficient patients. FIG. 7 depicts a typical dose dependent effect of factor VIII replacement in a patient whose baseline factor VIII level was less than 1%. As the VIII level is increased, the TGT shortens and both PCF and CEM increase. Mean values for increasing factor concentrations are recorded in Table 2.

Figure 8:
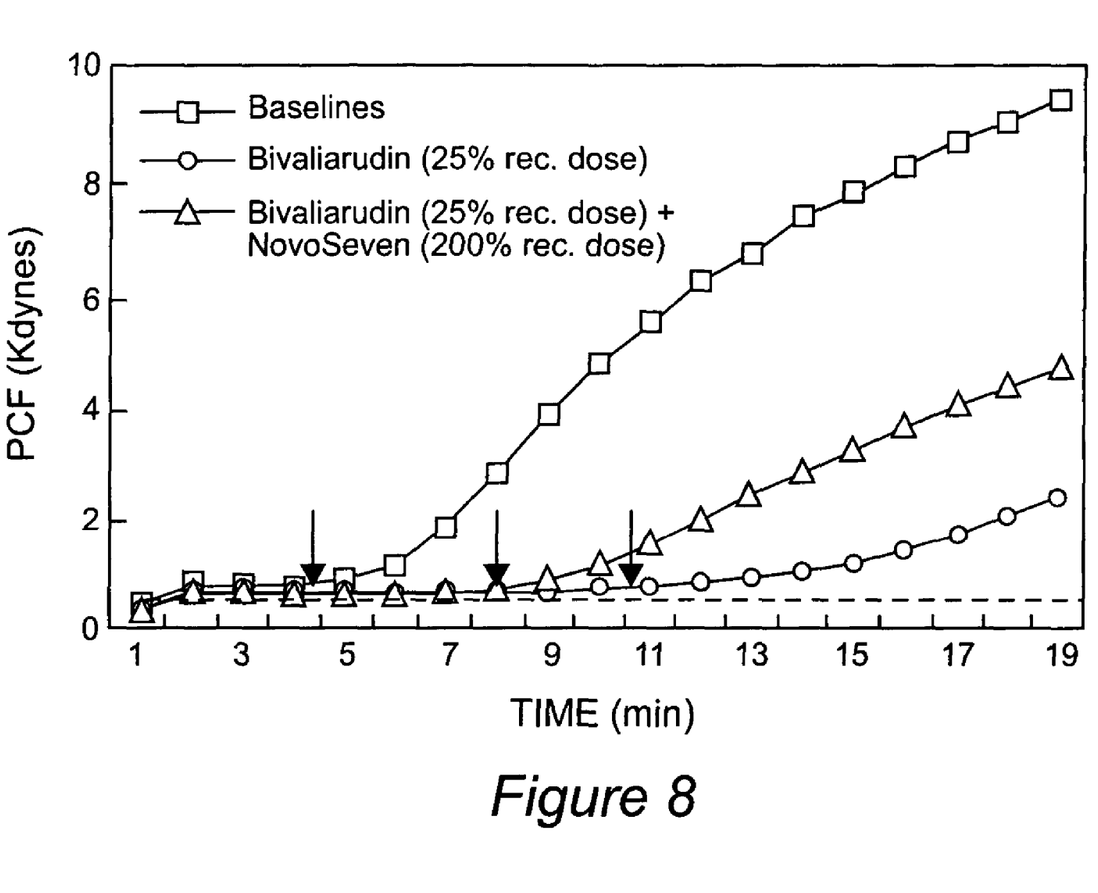
FIG. 8. Combined effects of a direct thrombin inhibitor (bivalirudin, The Medicines Company, Cambridge, Mass.) and recombinant factor VIIa (Novo Nordisk, Copenhagen, Denmark) on TGT and PCF in normal whole blood. The addition of bivalirudin (3.5 µg/ml) moves the curve to the right resulting in a prolonged TGT and a lower PCF. The addition of rVIIa (2.52 µg/ml) partially compensates by moving the curve back toward the left leading to shorter TGT and increased PCF.

Combined Effects of Anticoagulation (Bivalirudin) and rVIIa in Normal Blood:

The potential for monitoring the simultaneous effects of an anticoagulant and a hemostatic agent in the same sample of blood is depicted in FIG. 8. The baseline curve of PCF development is normal. When bivalirudin is added, the TGT prolongs and PCF decreases. If recombinant Factor VIIa (rVIIa) is added to the bivalirudin sample prior to clotting, both TGT and PCF improve toward normal. This same study indicated that at higher bivalirudin concentrations, rVIIa could not reverse the anticoagulant effect.

REFERENCES

1. Roberts H R, Monroe D M, Oliver J A, Chang J Y, Hoffman M. Newer concepts of blood coagulation. *Haemophilia*. 1998; 4: 331–334.
2. Butenas S, van't Veer C, Mann K G. "Normal" Thrombin Generation. *Blood.* 1999; 94:2169–2178.
3. Carr M E, Carr S L, Tildon T, Fisher L M, Martin E J. Batroxobin-induced clots exhibit delayed and reduced platelet contractile force in some patients with clotting factor deficiencies. *J Thromb Haemost.* 2003; 1: (in press).
4. Carr M E, Carr S L, Greilich P E. Heparin Ablates Force Development during Platelet Mediated Clot Retraction. *Thromb Haemost.* 1996;75:674–678.
5. Carr Jr M E, Angchaisuksiri P, Carr S L, Barnes J. Effect of antithrombin III concentrate, alone or with heparin, on clot structure and platelet function. *Blood.* 1995; 86 Suppl 1:866a.
6. Carr M E, Monge-Meberg P, McCardell K, Carr S L. Dermatan sulfate suppresses platelet force as it prolongs the APTT. *Blood.* 1996;88 Suppl 1:79b.
7. Carr M E, Zekert S L. Measurement of platelet mediated force development during plasma clot formation. *Am J Med Sci.* 1991;302: 13–18.
8. Carr ME. Measurement of platelet force: the Hemodyne Hemostasis analyzer. *Clin Lab Management Rev.* 1995; 9:312–320. 9.Carr M E, Carr S L. Abnormal clot retraction, altered fibrin structure and normal platelet function in multiple myeloma. *Am J Physiol.* 1994;266: H1195–1201.
10. de Gaetano G, Franco R, Donati M B, Bonaccorsi A, Garattini S. Mechanical recording of reptilase-clot retraction: effect of adenosine-5'-diphosphate and prostaglandin E₁. *Thromb Res.* 1974;4:189–192.
11. Boneu B. Low molecular weight beparin therapy: is monitoring needed? *Thromb Haemost.* 1994;72:330–334.
12. Hedner U, Ingerslev J. Clinical use of recombinant VIIa (rVIIa). *Transfus Sci.* 1998; 19: 163–176.
13. Vander Velden P, Giles A R. A detailed morphological evaluation of the evolution of the haemostatic plug in normal, factor VII and factor VIII deficient dogs. *Br J Haematol.* 1988;70:345–355
14. Hong yu N, Giles A R. Normalization of the haemostatic plugs of dogs with haemophilia A (factor VIII deficiency) following the infusion of a combination of factor Xa and phosphatidylcholine/phosphatidylserine vesicles. *Thromb Haemost.* 1992;67:264–271
15. Cawthern K M, van't Veer C, Lock J B, DiLorenzo M E, Branda R F, Mann K G.
  Blood coagulation in hemophilia A and hemophilia C. *Blood.* 199;91:4581–4592.
16. Carr M E Jr, Martin E J, Carr S L. Delayed, reduced or inhibited thrombin production reduces platelet contractile force and results in weaker clot formation. *Blood Coagul Fibrinolysis.* 2002;13:193–197.
17. Greilich P E, Carr M E, Zekert S L, Dent R M. Quantitative Assessment of Platelet Function and Clot Structure in Patients with Severe Coronary Artery Disease. *Am J Med Sci.* 1994; 307: 15–20.
18. Al-Obaidi M K, Philippou H, Stubbs P J, et al. Relationships between homocysteine, factor VIIa, and thrombin generation in acute coronary syndromes. *Circulation.* 2000;101:372–377.
19. Cushman M, Psaty B M, Macy E. Correlates of thrombin markers in an elderly cohort free of clinical cardiovascular disease. *Arterioscler Thromb Vasc Biol.* 1996;16: 1163–1169.
20. Aoki I, Shimoyama K, Aoki N. Platelet-dependent thrombin generation in patients with diabetes mellitus: effects of glycemic control on coagulability in diabetes. *J Am Coll Cardiol.* 1996;27:560–566.
21. Gruden G, Cavallo-Perin P, Romagnoli R, Olivetti C, Frezet D, Pagano G. Prothrombin fragment 1+2 and antithrombin UT-thrombin complex in microalbuminuric type 2 diabetic patients. *Diabet Med.* 1994; 11:485–488.
22. Butenas S, van't Veer C, Cawthern K, Brummel K E, Mann K G. Models of blood coagulation. *Blood Coagul Fibrinolysis.* 2000;11 Suppl 1:S9–13.
23. Butenas S, Mann K G. Blood coagulation. *Biochemistry* (Mosc). 2002;67:3–12.
24. Carr M E, Park A, Zekert S L, Marques D, Goldman I D, Sobel M. Anticoagulant and antiplatelet activities of heparin and low molecular weight derivatives. *Blood.* 1993; 82 Suppl 1:603a.
25. Carr M E, Zekert S. Effect of non-heparin thrombin antagonists on platelet force development during clot retraction. *Thromb Haemost.* 1993;69:1241.
26. Carr M E, Martin E J, Kuhn J G, Seremetis S V. Effects of recombinant factor VIIa on platelet function and clot structure in blood with deficient prothrombin conversion. *Thromb Haemost.* 2003; (in press).
27. Hemker H C, Giesen P L, Ramjee M, Wagenvoord R, Beguin S. The thrombogram: monitoring thrombin generation in platelet-rich plasma *Thromb Haemost.* 2000; 83:589–591.
28. Hartert H. Blutgerinnung studien mit der thrombelastographie, einen neuen untersuchingsverfahren. Klin Wochenschr. 1948;26:577–583.
29. Caprini J A, Traverso C I, Arcelus J I. Perspectives on thromboelastography. *Semin Thromb Hemost.* 1995;21 Suppl 4:91–93.
30. Spiess B D. Thromboelastography and cardiopulmonary bypass. *Semin Thromb Hemost.* 1995;21 Suppl 4:27–33.
31. Salooja N, Perry D J. Thrombelastography. *Blood Coagul Fibrinolysis.* 2001 ;12:327–337.
32. Yoshioka A, Nishio K, Shima M. Thrombelastgram as a hemostatic monitor during recombinant factor VIIa treatment in hemophilia A patients with inhibitor to factor VIII. Haemostasis. 1996;26 Suppl 1:139–142.

33. Cammerer U, Dietrich W, Rampf T, Braun S L, Richter J A. The predictive value of modified computerized thromboelastography and platelet function analysis for postoperative blood loss in routine cardiac surgery. *Anesth Analg.* 2003; 96:51–57.

34. Ingerslev J, Christiansen K, Calatzis A, Holm M, Sabroe Ebbesen L.
Management and monitoring of recombinant activated factor VII. *Blood Coagul Fibrinolysis.* 2000;11 Suppl 1: S25–30.

35. LaForce W R, Brudno D S, Kanto W P, Karp W B. Evaluation of the SonoClot Analyzer for the measurement of platelet function in whole blood. *Ann Clin Lab Sci.* 1992;22:30–33

36. Liszka-Hackzell J J, Ekback G. Analysis of the information content in Sonoclot data and reconstruction of coagulation test variables. *J Med Syst.* 2002;26:1–8.

37. Ramstrom S, Ranby M, Lindahl T L. The role of platelets in blood coagulation—effects of platelet agonists and GPIIb/IIIa inhibitors studied by free oscillation rheometry. *Thromb Res.* 2002; 105:165–172.

While the invention has been described in terms of its preferred embodiments, those skilled in the art will recognize that the invention can be practiced with modification within the spirit and scope of the appended claim.

I claim:

1. An assay for identifying a thrombin generation time for a blood sample, comprising the steps of:
   positioning a blood sample in an instrument which measures platelet contractile force; and
   determining onset of platelet contractile force in said blood sample, the onset of platelet contractile force being indicative of a thrombin generation time.

2. An assay for identifying delayed or deficient thrombin production in a patient, comprising the steps of:
   positioning a blood sample of a patient in an instrument which measures platelet contractile force;
   determining onset of platelet contractile force in said blood sample, the onset of platelet contractile being indicative of a thrombin generation time for said patient; and
   comparing said thrombin generation time to a normal range for thrombin generation time, whereby delayed or deficient thrombin production is identified when said thrombin generation time is greater than said normal range for thrombin generation time.

3. An assay for identifying increased thrombin production in a patient, comprising the steps of:
   positioning a blood sample of a patient in an instrument which measures platelet contractile force;
   determining onset of platelet contractile force in said blood sample, the onset of platelet contractile force being indicative of a thrombin generation time for said patient; and
   comparing said thrombin generation time to a normal range for thrombin generation time, whereby accelerated thrombin production is identified when said thrombin generation time is less than said normal range for thrombin generation time.

4. A method of treating blood disorders in a patient associated with thrombin generation, comprising the steps of:
   a) positioning a blood sample of a patient in an instrument which measures platelet contractile force;
   b) determining onset of platelet contractile force in said blood sample, the onset of platelet contractile force being indicative of a thrombin generation time for said patient;
   c) comparing said thrombin generation time to a normal range for thrombin generation time, whereby accelerated thrombin production is identified when said thrombin generation time is less than said normal range for thrombin generation time, and whereby delayed or deficient thrombin production is identified when said thrombin generation time is greater than said normal range for thrombin generation time; and
   d) when a comparison generated in step c) indicates said thrombin generation time is outside said normal range for thrombin generation time, then performing the steps of
      i) administering a therapeutic agent to said patient for adjusting said thrombin generation time, and
      ii) repeating steps a), b), and c).

5. The method of claim 4 further comprising the step of repeating step d) one or more times.

6. The method of claim 4 wherein said therapeutic agent is an anticoagulant.

7. The method of claim 4 wherein said therapeutic agent is a clotting factor.

8. The method of claim 4 wherein said therapeutic agent is an antiplatelet agent.

* * * * *